United States Patent [19]

Halm et al.

[11] Patent Number: 4,965,388
[45] Date of Patent: Oct. 23, 1990

[54] METHOD FOR PREPARING ORGANOHALOSILANES

[75] Inventors: Roland L. Halm, Madison, Ind.; Regie H. Zapp, Carrollton, Ky.; Rick D. Streu, Midland, Mich.

[73] Assignee: Dow Corning Corporation, Midland, Mich.

[21] Appl. No.: 459,630

[22] Filed: Jan. 2, 1990

[51] Int. Cl.$^5$ .............................................. C07F 7/16
[52] U.S. Cl. .................................................... 556/472
[58] Field of Search ......................................... 556/472

[56] References Cited

U.S. PATENT DOCUMENTS

| | | | |
|---|---|---|---|
| 2,380,996 | 8/1945 | Rochow et al. | 556/472 |
| 2,380,997 | 8/1945 | Patnode | 556/472 |
| 2,380,999 | 8/1945 | Sprung et al. | 556/472 |
| 2,383,818 | 8/1945 | Rochow et al. | 556/472 |
| 3,133,109 | 5/1964 | Dotson | 556/472 |
| 4,218,387 | 8/1980 | Maas et al. | 556/472 |
| 4,500,724 | 2/1985 | Ward et al. | 556/472 |
| 4,602,101 | 7/1986 | Halm et al. | 556/472 |
| 4,645,851 | 2/1987 | Prud'Homme | 556/472 |
| 4,656,301 | 4/1987 | Prud'Homme et al. | 556/472 |
| 4,661,613 | 4/1987 | Prud'Homme | 556/472 |
| 4,684,741 | 8/1987 | Prud'Homme | 556/472 |

FOREIGN PATENT DOCUMENTS 1089726 9/1966 United Kingdom ................ 556/472

OTHER PUBLICATIONS

Elsevier (1967), Chpt. 4, "General Principles of the Direct Synthesis of Methylhalosilanes and Other Organohalosilanes", pp. 120–185.
Csakvari, et al, Acta Chim. Acad. Sci. Hung. 39 (1), 33–7 (1963).
Rathousky, et al, (1972), pp. 485–488.
De Cooker, et al, J. Org. Chem., 99(1975), 371–377, "Direct Synthesis of Methyldichlorosilane and Dimethylchlorosilane".

Primary Examiner—Paul F. Shaver
Attorney, Agent, or Firm—Robert Spector

[57] ABSTRACT

The present invention provides a method for reducing the concentration of methyltrichlorosilane obtained during the reaction of silicon metal with methyl chloride without substantially decreasing the combined yield of methyldichlorosilane, dimethylchlorosilane and dimethyldichlorosilane. The methyl chloride is blended with from 0.05 up to about 44 mole percent of hydrogen, based on combination of methyl chloride and hydrogen. At hydrogen concentrations above about 12 mole percent there is a substantial increase in the methyldichlorosilane content of the reaction product while the concentration of methyltrichlorosilane in the reaction product is maintained below about 4 percent by weight.

13 Claims, No Drawings

METHOD FOR PREPARING ORGANOHALOSILANES

BACKGROUND OF THE INVENTION

This invention relates to the preparation of organohalosilanes. More particularly, this invention relates to reducing the yield of undesired monoorganotrichlorosilane produced when preparing organochlorosilanes using a method referred to in the art as the "direct process". This reduction is accomplished without either adversely affecting the yield of other desirable organochlorosilanes, particularly the diorganodichlorosilane, or generating substantial quantities of undesirable inorganic chlorosilanes and organochlorosilanes.

A second embodiment of this invention provides a method for achieving all of the foregoing objectives while increasing the yield of the corresponding monoorganodichlorosilane.

DESCRIPTION OF RELEVANT ART

The preparation of organohalosilanes by the reaction of an alkyl or aryl halide with silicon metal in the presence of various catalysts is known as the "direct process". The halide portion is typically chlorine, but can also be bromine or iodine.

Application of the direct process to the preparation of organohalosilanes was first disclosed by Rochow and his co-workers, beginning in the mid-1940's. The art describes numerous improvements to this direct process.

Rochow and Patnode, U.S. Pat. No. 2,380,996, issued Aug. 7, 1945, and Patnode, U.S. Pat. No. 2,380,997, issued Aug. 7, 1945, disclose the preparation of a contact mass for the direct process. The mass is prepared by firing a mixture of silicon copper, or other metallic catalysts in a reducing atmosphere. Rochow and Patnode and Patnode also disclose the use of nickel, tin, antimony, manganese, silver, and titanium.

Rochow and Gilliam, U.S. Pat. No. 2,383,818, issued Aug. 28, 1945, discloses the use of contact masses comprising silicon and an oxide of copper. Also, included are copper compounds which are readily converted to the oxides, such as copper nitrate An example of more recent art is Chapters 4 and 5 of a text entitled Organohalosilanes by R. J. H. Voorhoeve, published in 1967 by Elsevier.

For various reasons, including cost and availability of starting materials, alkylchlorosilanes, particularly methyl- and ethylchlorosilanes, have become the organohalosilanes most frequently prepared by the direct process. The present invention has therefore been described by reference to this class of alkylchlorosilanes using the corresponding alkyl chlorides. It should be understood that while preferred embodiments of the present invention are directed primarily to the preparation of certain methylchlorosilanes by reacting methyl chloride and silicon, the invention is not to be so limited.

When methyl chloride, represented by the formula MeCl, and silicon metal are reacted using the catalysts and reaction conditions described in the prior art, the resultant products include but are not limited to MeHSiCl$_2$, Me$_2$SiCl$_2$, Me$_3$SiCl, MeSiCl$_3$, Me$_2$HSiCl, HSiCl$_3$ and SiCl$_4$, where Me represents the methyl radical. By an appropriate selection of catalyst and reaction conditions it is possible to obtain dimethyldichlorosilane, Me$_2$SiCl$_2$, as the major component, often 90 weight % or more, in the final product mixture. Methyldichlorosilane, MeHSiCl$_2$ typically constitutes about 1 weight percent of the product under these conditions, which are designed to optimize the yield of Me$_2$SiCl$_2$. The reaction product also typically contains a significant concentration of methyltrichlorosilane, MeSiCl$_3$, which in many instances is not a desired product.

The prior art does not provide a method for decreasing the relative amount of methyltrichlorosilane in a direct process product mixture without a substantial decrease in the yield of dimethyldichlorosilane.

It is known to blend the methyl chloride with five weight percent or more, based on methyl chloride, of hydrogen as a means for increasing the relative yield of methyldichlorosilane in the final product, however the yield of dimethyldichlorosilane is more than correspondingly reduced and substantial quantities of undesirable organic chlorosilanes are produced.

U.S. Pat. No. 2,380,999 which issued to Sprung et al on Aug. 7, 1945 teaches sintering a mixture containing 90 weight percent silicon and 10 weight percent copper for one hour at 1050°C. under a hydrogen atmosphere. The resultant reaction mass is then placed in a stream of methyl chloride flowing at a rate of 80 cc. per minute. Following separation of volatile materials the liquid reaction product was found to contain 73.5 weight percent dimethyldichlorosilane, 9 percent methyltrichlorosilane, 6 weight percent trimethylchlorosilane, and "small amounts of other methylchlorosilanes". Combining the methyl chloride with nitrogen increased the yield of dimethyldichlorosilane to 86.5 percent, the only other specifically reported product being 4.0 weight percent of methyltrichlorosilane.

An article by Csakvari et al. that appeared in Acta Chim. Acad. Sci. Hung. 39 (1), 33-7 (1963) mentions prior art disclosing the use of methyl chloride/hydrogen mixtures to achieve a 20 weight percent yield of methyldichlorosilane in the final product. The types and amounts of other methylchlorosilanes produced are not disclosed.

British patent no. 1,089,726, which issued to Morozov et al. on Nov. 8, 1967 teaches obtaining up to a 65 weight percent yield of methyldichlorosilane based on total reaction product, or up to a 16 weight percent yield of dimethylchlorosilane by adding iron, cobalt, nickel, or their salts to the silicon/copper reaction mass in a direct process and blending the methyl chloride with hydrogen. The rates of addition of hydrogen and methyl chloride are each from 0.1 to 0.5 liters per minute. The products described in the examples of this patent contain from 13 to 33 weight percent of methyltrichlorosilane.

An article by J. Rathousky et al. [Chem. Prum., 22(10) 485-8 (1972)] discusses the effect of hydrogen addition on the product distribution obtained from the reaction of methyl chloride with a 9:1 weight ratio mixture of silicon and copper under superatmospheric pressure at a temperature of 320° C. The yield of methyldichlorosilane increased by a factor of 5 and the yield of dimethyldichlorosilane decreased proportionately as the hydrogen concentration was increased from 0 to 15 mole percent of a methyl chloride/hydrogen mixture. The yield of methyltrichlorosilane ranged from 24.2 to 38.1 weight percent of the total product over the range of hydrogen concentrations investigated. The combined yield of methyldichlorosilane and dimethyldichlorosilane constituted from 50 to 66 weight percent of the reaction product at all hydrogen concentrations and reaction conditions, and the reaction product contained small amounts of dichlorosilane, trichlorosilane, silicon tetrachloride and trimethylchlorosilane.

The effect of varying amounts of hydrogen on the direct process reaction using a copper catalyst is reported by M. De Cooker et al in the Journal of Organometallic Chemistry, 99(1975) 371-377. During the five experimental runs the partial pressure of hydrogen was varied from 0.55 to 0.75 atmosphere, equivalent to from 55 to 75 mole percent hydrogen under conditions of standard temperature and pressure, and the combined pressure of hydrogen and the methyl chloride reactant totaled one atmosphere. The highest yield of dimethyldichlorosilane reported is 88 mole percent, and the corresponding yields of methyldichlorosilane and trimethylchlorosilane were 4 mole percent each.

Methods for increasing the yields of dimethyldichlorosilane and methyldichlorosilane while reducing the yield of methyltrichlorosilane obtained using the direct process are described in the prior art. For example, U.S. Pat. No. 4,500 724, which issued to Ward et al. on Feb. 19, 1985 teaches using catalytic amounts of copper zinc and tin to increase the yield of dimethyldichlorosilane and reduce the ratio of methyltrichlorosilane to dimethyldichlorosilane obtained from a direct process reaction. The weight ratio of methyltrichlorosilane to dimethyldichlorosilane reported in the examples of this patent is from 0.041 to 0.099. The lowest yield of methyltrichlorosilane achieved by following the teaching of this patent is 4 percent by weight, based on the yield of dimethyldichlorosilane.

An objective of the present invention is to provide a method for decreasing to below about 4 weight percent the concentration of methyltrichlorosilane in the product obtained from the reaction of silicon with methyl chloride, and to achieve this without substantially reducing the yield of dimethyldichlorosilane. The objective of a second embodiment of this invention is to maintain this reduced level of methyltrichlorosilane while increasing the yield of methyldichlorosilane and dimethylchlorosilane.

SUMMARY OF THE INVENTION

The present invention is based on the discovery that when amounts of hydrogen smaller than reported in the relevant literature are blended with methyl chloride and the resultant mixture is reacted with silicon metal in the presence of a suitable catalyst to form methylchlorosilanes, the yield of undesirable methyltrichlorosilane is reduced without adversely affecting the yield of desirable products, particularly dimethyldichlorosilane.

DETAILED DESCRIPTION OF THE INVENTION

One embodiment of this invention provides a method for reducing the concentration of methyltrichlorosilane without substantially decreasing the concentration of dimethyldichlorosilane in the mixture of methylchlorosilanes produced by the addition of methyl chloride to a reactor containing a reaction mass comprising silicon metal and a suitable catalyst at a temperatures of from 250° to about 350° C. The method comprises homogeneously blending the methyl chloride with from 0.5 to 12 mole percent of hydrogen, based on methyl chloride and hydrogen. The reaction is preferably conducted in the presence of a catalytic amount of copper in combination with at least one of tin and zinc. These elements can be present in the form of the metals or compounds of the metals.

A second embodiment of this invention provides a method for increasing the concentrations of methyldichlorosilane and dimethylchlorosilane without substantially reducing the combined concentration of these products and dimethyldichlorosilane that is produced during the reaction of methyl chloride with silicon as described in the preceding paragraph. This method comprises homogeneously blending the methyl chloride with from 12 to 44 mole percent of hydrogen, based on methyl chloride and hydrogen, in the presence of an effective amount of a catalyst capable of maintaining the concentration of methyltrichlorosilane in the reaction product below about 4 percent by weight. Copper in combination with at least one of tin and zinc is the preferred catalyst for this reaction.

Determination of Optimum Hydrogen Concentrations

In accordance with the first embodiment of this invention, the concentration range of hydrogen in the methyl chloride reactant that will reduce the yield of methyltrichlorosilane without reducing the concentration of dimethyldichlorosilane, $(CH_3)_2SiCl_2$, in the reaction product will depend at least to some extent, on the conditions under which the methyl chloride and silicon metal are reacted. These conditions include but are not limited to the presence of catalyst(s) and reaction promoters, temperature, purity of the reactants, and the configuration and size of the reactor.

The optimum hydrogen concentration range for a given set of reaction conditions can be determined with a minimum of experimentation by those of ordinary skill in the art of organohalosilane preparation having knowledge of the present invention.

Specifically, using a preferred set of reaction conditions and catalyst compositions described in the subsequent section of this specification, a surprisingly large reduction in the yield of methyltrichlorosilane is achieved using as little as 0.5 mole percent of hydrogen, based on the combination of hydrogen and methyl chloride (equivalent to 0.02 weight percent of hydrogen, based on methyl chloride). The yield of methyltrichlorosilane decreases with increasing hydrogen concentration up to a level about 12 mole percent (0.5 weight percent of hydrogen, based on methyl chloride). This is accompanied by small increases in the concentrations of methyldichlorosilane and dimethylchlorosilane.

When the hydrogen concentration in a direct process reaction is increased from about 12 mole percent up to about 44 mole percent (3 weight percent hydrogen, based on methyl chloride), the prior art discussed is a preceding section of this specification shows a substantial increase in the yield of methyldichlorosilane that is proportional to the hydrogen concentration. The shortcoming of these prior art processes is that the increase in methyldichlorosilane is accompanied by a relatively high concentration of methyltrichlorosilane, which is typically an undesirable by-product.

The present inventors have discovered that, in the presence of certain catalyst compositions, methyltrichlorosilane constitutes less than 4 weight percent of the reaction product while the combined yield of methyldichlorosilane, dimethylchlorosilane and dimethyldichlorosilane exceeds 90 weight percent of the reaction mixture. Suitable catalysts include the mixtures of copper with at least one of tin and zinc that are described in detail in the following section of this specification as preferred catalysts for use in the present method. This method for increasing the yield of methyldichlorosilane and dimethylchlorosilane constitutes the second embodiment of the present invention.

Above a hydrogen concentration of 44 mole percent the yields of both methyldichlorosilane and dimethyldichlorosilane begin to decrease.

In addition to decreased yields of methyldichlorosilane and dimethyldichlorosilane, a second reason for not using relativelY large concentrations of hydrogen in the present method is that only a small fraction of the hydrogen reacts. The remainder must be either vented or recycled. The presence of unreacted hydrogen in combination with a number of other materials, including unreacted methyl chloride, may make recycling of the effluent gas stream economically unattractive and venting of large volumes of the gas stream hazardous. A third reason is a reduction in the quantity of silicon converted during the reaction. For these three reasons the upper concentration limit for hydrogen in the methyl chloride stream is about 44 mole percent.

Reaction Catalysts and Promoters

The combination of a high yield of dimethyldichlorosilane and a reduction in the concentration of methyltrichlorosilane achieved using the present method is believed due to (1) the mixture of hydrogen and methyl chloride that is reacted with silicon and (2) the presence of a catalyst composition that will suppress the formation of methyltrichlorosilane during this reaction.

CatalYsts suitable for use in the present method include but are not limited to copper or a copper compound in combination with at least one of tin and zinc. The tin and zinc can be in the form of the metals or compounds of these metals.

The art pertaining to the direct process for preparing alkylhalosilanes discloses a variety of catalysts and promoters suitable for use in the direct process. The aforementioned U.S. Pat. No. 4,500,724 to Ward et al. discloses catalysts for the production of organohalosilanes comprising copper and copper oxides, tin or tin containing compounds, and zinc or zinc-containing compounds. In accordance with the teaching of this patent the concentration of methyltrichlorosilane in a silicon/-methyl chloride reaction product is reduced using specified ratios of copper, zinc and tin as the catalyst for the reaction.

Halm et al. in U.S. Pat. No. 4,602,101. issued July 22, 1986, discloses catalysts for controlling product selectivity and increasing silicon conversion during the reaction of an alkyl halide with metallurgical grade silicon, at a temperature of 250°–350° C. The catalysts for this reaction are combinations of copper or a copper compound with tin or a tin compound. The reaction mass also contains phosphorous or phosphorous-containing compounds as reaction promoters. The concentration of phosphorus or phosphorus compound is from 25 to 2500 parts by weight per million parts (ppm) of initial reaction mass, the concentration of copper is from 0.2 to 10 weight percent, based on the initial weight in the reaction mass and the concentration of tin is from 5 to 200 ppm. The concentration limits on phosphorus, copper and tin disclosed in the aforementioned patent to Halm et al. also apply to the reaction mixtures of the present invention. The reaction mass can also contain up to about one weight percent each of aluminum and/or iron based on weight of initial silicon.

Additional suitable catalysts and promoters that can be combined with copper in accordance with the present method include but are not limited to at least one of zinc, calcium, barium, titanium, zirconium, cadmium, lead, bismuth, arsenic, nickel, antimony silver, and cobalt. Any of these promoters can be used in its elemental form or as compounds or alloys that contain the element.

Preferred catalyst/promoter compositions include but are not limited to:

1.(a) Copper or a copper compound and (b) zinc or a zinc compound;

2. (a) Copper or a copper compound, (b) zinc or a zinc compound and (c) tin or a tin compound;

3. (a) Copper or a copper compound, (b) tin or a tin compound, and (c) optionally arsenic or an arsenic compound;

4. (a) Copper in the form of a mixture, alloy or compound. (b) at least one member selected from the group consisting of tin, tin compounds, zinc and zinc compounds, and (c) at least one member selected from the group consisting of phosphorus, phosphorus compounds, phosphorus-containing alloys, and metal phosphides;

5. (a) Copper or a copper compound, (b) tin or a tin compound, (c) arsenic or an arsenic compound, and (d) phosphorus or a phosphorus compound;

6. (a) Iron alloyed with silicon or an alloy of silicon, iron and aluminum, where the concentrations of iron and aluminum do not exceed about one weight percent, based on weight of initial silicon, (b) copper or at least one copper compound, and optionally at least one member selected from the group consisting of tin, tin compounds, zinc, zinc compounds, elemental phosphorus, metal phosphides, and phosphorus-containing alloys; and 7. (a) A mixture of copper and zinc that is present as brass. (b) cuprous chloride, (c) tin and/or at least one tin compound and (d) a metal-phosphorus alloy.

The metal portion of the metal-phosphorus alloy or phosphide is preferably aluminum, calcium, copper, or zinc.

The present catalysts and promoters are typically used in amounts as low as several parts per million. Unless otherwise specified in the preceding specification, up to 10 weight percent, based on initial reaction mass, of many of the aforementioned catalysts can be used.

For best results, the purity of the silicon should be at least 95% but less than 100%. A metallurgical grade of silicon is preferred. For optimum results the silicon is in a particulate form.

Reaction Conditions and Equipment

The optimum hydrogen concentration range is at least partially dependent on the type of equipment and reaction conditions used in practicing the present method. Suitable equipment for conducting the direct process include fixed bed, stirred bed and fluid bed reactors. Any of these reactors can be operated in a continuous or batch mode.

It is within the scope of the present invention to utilize the reactor described in U.S. Pat. No. 3,133,109, which issued to Dotson on May 12, 1964 or the one described by Maas et al. in U.S. Pat. No. 4,218,387.

The particle size of the fluidized material should be within the range typically used for the direct process. The aforementioned Dotson patent discloses a particle size range of from 20 to 200 microns. Depending upon the capacity of the reactor, a range of from 1 to 200 microns is preferred for the present method.

The temperature range used for the direct process is typically from 250° to about 350° C. Temperatures within the range of from 260° to about 330° C. are preferred to optimize yields of the desired methylchlorosilanes.

EXAMPLES

The following examples describe preferred embodiments of the present invention with respect to types and concentrations of reactants, catalysts, promoters, process conditions and equipment, and should not be interpreted as limiting the present invention as defined in the accompanying claims. Unless otherwise indicated all parts and percentages in the example are by weight, all quantities expressed in parts per million are based on the weight of all materials initially charged to the reactor together with the silicon, and all prior art mentioned is incorporated by reference thereto.

GENERAL PROCEDURE

The reaction between silicon and methyl chloride was conducted in a fluidized bed reactor of the type described in U.S. Pat. No. 3,133,109 to Dotson. The temperature of the sand bath used to heat the reactor was 315° C. and each heating period, equivalent to the reaction time, was 44 hours in duration.

Metallurgical grade silicon (Globe Metallurgical, Inc. Beverly, Ohio) was employed which contained aluminum (0.22%), calcium (0.046%), and iron (0.34%). The hydrogen was of 99.999% minimum purity, obtained from Matheson Gas Products Dayton, Ohio. The methyl chloride and hydrogen were individually metered using calibrated flowmeters. When hydrogen was used the gas streams were combined and passed through a static mixer to ensure proper blending prior to being introduced into the reactor.

The material used as the reaction mass was prepared by blending the following ingredients to homogeneity in a suitable container: 100 parts of silicon, 6.48 parts of cuprous chloride, 600 parts per million (ppm) brass (a 1/1 weight ratio alloy of copper and zinc), 30 ppm tin and 2000 ppm of a copper phosphorus alloy containing 13.5 weight percent phosphorus. The resultant mixture of ingredients was homogenized by shaking it vigorously for 2 to 3 minutes. This mixture was then charged to the reactor, following which the reactor was closed and placed in the 315° C., sand bath. At this time a stream of nitrogen was passed through the reactor as a fluidizing medium. The sand bath was continuously fluidized to maintain a constant temperature within the reactor.

When the temperature of the reactor reached about 315° C. the nitrogen was replaced with a stream of gaseous methyl chloride as the fluidizing medium. The flow of methyl chloride was continued for 44 hours. When hydrogen was added it was blended with the methyl chloride throughout the entire methyl chloride addition.

The products emerging from the reactor were condensed and collected in previously weighed cold traps. The liquid collected in the traps was then transferred to cooled bottles and then injected into the sample chamber of a gas chromatograph using a previously cooled syringe. The chromatograph was used to determine the types and concentration of reaction products.

EXAMPLE 1

Control Example

This example typifies the product distribution obtained in the absence of hydrogen.

The product distributions from two runs performed without the addition of hydrogen were determined and the results were averaged. The averaged values, reported here and summarized in Table 1, were:

91.9% Dimethyldichlorosilane ($Me_2SiCl_2$)
1.3% Methyldichlorosilane ($MeHSiCl_2$)
0.2% Dimethylchlorosilane ($Me_2HSiCl$)
4.1% Methyltrichlorosilane ($MeSiCl_3$)

The remaining material was a mixture of other methylchlorosilanes. There were no detectable amounts of $HSiCl_3$ or $SiCl_4$ present.

EXAMPLE 2

This example demonstrates the advantages of blending from 0.2 to 5 weight percent of hydrogen with the methyl chloride reactant. Using the General Procedure described in the foregoing specification the amounts of hydrogen listed in Table 1 were blended with the methyl chloride throughout the entire methyl chloride addition. The concentration of hydrogen in the methyl chloride stream and concentrations of four of the principal products are shown in the following table. The product concentrations are based on an average of two runs. The table includes data from two sets of two runs using a hydrogen concentration of 1 percent.

The remaining material in the reaction product was a mixture of other methylchlorosilanes. No detectable amounts of inorganic silicon halides were produced.

The data reported in Table 1 demonstrate that (1) the concentration of methyltrichlorosilane is substantially reduced from 4.1 weight percent to 2.9 weight percent at hydrogen concentrations of 0.0 and 0.2 weight percent, respectively, and (2) there is a substantial increase in the yield of $MeHSiCl_2$ at a hydrogen concentration of 0.45 weight percent.

At a hydrogen content of 3 weight percent the concentration of methyldichlorosilane increased to 14.1 percent, with only a 3 percent decrease in the combined yield of this silane and dimethyldichlorosilane relative to the combined yield in the absence of hydrogen, and an increase in the combined yield of $Me_2SiCl_2$, $MeHSiCl_2$ and $Me_2HSiCl$. The concentration of methyltrichlorosilane decreased from 4.1 percent in the absence of hydrogen to 2.1 percent using from 1 to 3 percent hydrogen in the methyl chloride feed.

TABLE 1

| H₂ added | | Products (Weight % of Total Product) | | | | |
|---|---|---|---|---|---|---|
| | | Desired | | | Combined | Undesired |
| (Mole %)** | (Wt %)** | Me₂SiCl₂ | MeHSiCl₂ | Me₂HSiCl | Yield* | MeSiCl₃ |
| 0 | 0.00 | 92.1 | 1.3 | 0.3 | 93.7 | 4.1 |
| 6 | 0.20 | 92.2 | 1.6 | 0.7 | 94.5 | 2.9 |
| 12 | 0.45 | 90.7 | 3.2 | 1.0 | 94.9 | 2.9 |
| 21 | 1.00*** | 81.6 | 10.2 | 4.3 | 96.1 | 2.1 |
| 21 | 1.00*** | 84.9 | 8.4 | 2.8 | 96.1 | 2.1 |
| 44 | 3.00 | 77.2 | 14.1 | 4.4 | 95.7 | 2.1 |
| 57 | 5.00 | 76.2 | 13.6 | 6.3 | 96.1 | 1.8 |

*Me₂SiCl₂, MeHSiCl₂ and Me₂HSiCl
**Mole % H₂ = (Moles H₂/(moles MeCl + Moles H₂)] × 100; Weight % H₂ = Weight H₂/Weight MeCl × 100
***Two sets of two runs each at the 1 percent level

What is claimed is:

1. In a method for producing a mixture of a methylchlorosilanes by the addition of methyl chloride to a reactor containing a reaction mass comprising silicon metal and a suitable catalyst at a temperatures of from 250° to about 350° C., the improvement consisting essentially of homogeneously blending said methyl chloride with an amount of hydrogen equivalent to from 0.5 to 12 mole percent, based on the combination of methyl chloride and hydrogen, to reduce the concentration of methyltrichlorosilane without substantially decreasing the concentration of dimethyldichlorosilane in the mixture.

2. A method according to claim 1 wherein the reaction between the methyl chloride and silicon is conducted at a temperature of from 260° to about 330° C. in the presence of a catalyst comprising copper or a copper compound and at least one member selected from the group consisting of tin, tin compounds, zinc and zinc compounds.

3. A method according to claim 2 where the concentration of copper is from 0.2 to 10 weight percent, the concentration of tin is from 5 to 200 ppm and the concentration of zinc is from 10 to 10,000 ppm, the concentrations being based on initial reaction mass.

4. A method according to claim 2 where the yield of methyltrichlorosilane does not exceed four percent of the combined weight of methylchlorosilanes produced in accordance with said method and said reaction mass includes a reaction promoter.

5. A method according to claim 4 where the combination of catalyst and reaction promoter is selected from the group consisting of
  copper or a copper compound and zinc or a zinc compound;
  copper or a copper compound zinc or a zinc compound and tin or a tin compound;
  copper or a copper compound and tin or a tin compound;
  copper or a copper compound, tin or a tin compound and arsenic or an arsenic compound;
  copper in the form of a mixture, alloy or compound, at least one member selected from the group consisting of tin, tin compounds, zinc and zinc compounds, and at least one member selected from the group consisting of phosphorus, phosphorus compounds, metal-phosphorus alloys and metal phosphides;
  copper or a copper compound, tin or a tin compound, arsenic or an arsenic compound and phosphorus or a phosphorus compound;
  iron alloyed with silicon or an alloy of iron, aluminum and silicon, and either copper or at least one copper compound;
  iron alloyed with silicon or an alloy of iron, aluminum and silicon, either copper or at least one copper compound, and at least one member selected from the group consisting of tin, tin compounds, elemental phoSphorus, metal phosphides, metal-phosphorus alloys, zinc and zinc compounds; and
  a mixture of copper and zinc that is present as brass, cuprous chloride, tin and tin compounds and metal-phosphorus alloy;
  where and the concentrations of iron and aluminum do not exceed 1 weight percent, based on the initial weight of silicon.

6. A method according to claim 5 where the metal portion of the metal phosphorus alloy or phosphide is aluminum, calcium, copper, or zinc.

7. In a method for increasing the concentration of methyldichlorosilane in a mixture of methylchlorosilanes produced by the addition of methyl chloride to a reactor containing a reaction mass comprising silicon metal and a suitable catalyst at a temperature of from 250° to about 350° C. said method comprising homogeneously blending the methyl chloride with hydrogen, the improvement comprising blending the methyl chloride with an amount of hydrogen equivalent to from 12 to 44 mole percent based on the combination of methyl chloride and hydrogen.

8. A method according to claim 7 where was said catalyst is selected from the group consisting of copper in combination with at least one member of the group consisting of tin, tin compounds, zinc and zinc compounds.

9. A method according to claim 8 where the concentration of copper is from 0.2 to 10 weight percent, the concentration of tin is from 5 to 200 ppm and the concentration of zinc is from 10 to 10,000 ppm, the concentrations being based on the weight of silicon in the initial reaction mass.

10. A method according to claim 7 wherein the reaction between the methyl chloride and silicon is conducted at a temperature of from 260° to about 330° C., and the combined yield of dimethyldichlorosilane and methyldichlorosilane is at least 90%.

11. A method according to claim 7 where the yield of methyltrichlorosilane does not exceed four percent of the combined weight of methylchlorosilanes produced in accordance with said method and the reaction mass includes a reaction promoter.

12. A method according to claim 8 where the combination of catalyst and reaction promoter is selected from the group consisting of copper or a copper compound and zinc or a zinc compound;

copper or a copper compound, zinc or a zinc compound and tin or a tin compound;

copper or a copper compound and tin or a tin compound;

copper or a copper compound, tin or a tin compound and arsenic or an arsenic compound;

copper in the form of a mixture, alloy or compound, at least one member selected from the group consisting of tin, tin compounds, zinc and zinc compounds, and at least one member selected from the group consisting of phosphorus, phosphorus compounds, phosphorus-containing alloys and metal phosphides;

copper or a copper compound, tin or a tin compound, arsenic or an arsenic compound and phosphorus or a phosphorus compound;

iron alloyed with silicon or an alloy of iron, aluminum and silicon, and either copper or at least one copper compound;

iron alloyed with silicon or an alloy of iron, aluminum and silicon, either copper or at least one copper compound, and at least one member selected from the group consisting of tin, tin compounds, elemental phosphorus, metal phosphides, phosphorus-containing alloys, zinc and zinc compounds; and a mixture of copper and zinc that is present as brass, cuprous chloride, tin and tin compounds and metal-phosphorus alloy, where the concentrations of iron and aluminum do not exceed one weight percent, based on the initial weight of silicon.

13. A method according to claim 12 where the metal portion of said metal phosphorus alloy or phosphide is aluminum, calcium, copper or zinc.

* * * * *